United States Patent
Ryu et al.

(10) Patent No.: US 10,766,842 B2
(45) Date of Patent: Sep. 8, 2020

(54) ANHYDROSUGAR ALCOHOL COMPOSITION HAVING ENHANCED STORAGE STABILITY, AND ANHYDROSUGAR ALCOHOL STORAGE METHOD

(71) Applicant: SAMYANG CORPORATION, Seoul (KR)

(72) Inventors: Hoon Ryu, Daejeon (KR); Seung Hyun Yoo, Daejeon (KR); Hyun Seung Lee, Incheon (KR); Jun Seop Im, Daejeon (KR); Young Jae Jung, Daejeon (KR)

(73) Assignee: SAMYANG CORPORATION, Seoul (KR)

( * ) Notice: Subject to any disclaimer, the term of this patent is extended or adjusted under 35 U.S.C. 154(b) by 8 days.

(21) Appl. No.: 15/779,688

(22) PCT Filed: Oct. 25, 2016

(86) PCT No.: PCT/KR2016/011997
§ 371 (c)(1),
(2) Date: May 29, 2018

(87) PCT Pub. No.: WO2017/095018
PCT Pub. Date: Jun. 8, 2017

(65) Prior Publication Data
US 2019/0284121 A1    Sep. 19, 2019

(30) Foreign Application Priority Data

Nov. 30, 2015 (KR) .................... 10-2015-0169260

(51) Int. Cl.
*C07C 29/94* (2006.01)
*C07C 29/84* (2006.01)
*A61K 31/34* (2006.01)
*C07C 31/26* (2006.01)
*A61K 8/49* (2006.01)
*A61K 47/18* (2017.01)
*C07D 493/04* (2006.01)

(52) U.S. Cl.
CPC ............... *C07C 29/94* (2013.01); *A61K 8/49* (2013.01); *A61K 31/34* (2013.01); *A61K 47/18* (2013.01); *C07C 29/84* (2013.01); *C07C 31/26* (2013.01); *C07D 493/04* (2013.01)

(58) Field of Classification Search
CPC ...................................................... C07C 29/84
USPC .......................................................... 568/701
See application file for complete search history.

(56) References Cited

U.S. PATENT DOCUMENTS

| | | |
|---|---|---|
| 2003/0097028 A1 | 5/2003 | Fuertes |
| 2008/0213439 A1 | 9/2008 | Fuertes |
| 2015/0299216 A1 | 10/2015 | Ryu et al. |
| 2017/0036747 A1 | 2/2017 | Gildehaus, III |

FOREIGN PATENT DOCUMENTS

| | | |
|---|---|---|
| JP | 5379016 B2 | 12/2013 |
| KR | 10-0939431 B1 | 1/2010 |
| KR | 10-2011-0076268 A | 7/2011 |
| KR | 10-2012-0066904 A | 6/2012 |
| KR | 10-2014-0105191 A | 9/2014 |
| KR | 10-2014-0108625 A | 9/2014 |
| KR | 10-2015-0091985 A | 8/2015 |
| KR | 10-1624571 B1 | 5/2016 |
| WO | WO 2009/057609 A1 | 5/2009 |

OTHER PUBLICATIONS

Machine translation KR20150091985, 2015.*
International Search Report issued in PCT/KR2016/011997 (PCT/ISA/210), dated Jan. 26, 2017.

* cited by examiner

*Primary Examiner* — Ana Z Muresan
(74) *Attorney, Agent, or Firm* — Birch, Stewart, Kolasch & Birch, LLP

(57) ABSTRACT

The present invention relates to an anhydrosugar alcohol composition having enhanced storage stability, and an anhydrosugar alcohol storage method, and more specifically, to an anhydrosugar alcohol composition having enhanced storage stability by comprising anhydrosugar alcohol and an amine-based additive; and to a method by which anhydrosugar alcohol having excellent quality may be provided by having the storing of the anhydrosugar alcohol performed under the existence of the amine-based additive, thereby remarkably enhancing the storage stability of the anhydrosugar alcohol.

11 Claims, No Drawings

ANHYDROSUGAR ALCOHOL COMPOSITION HAVING ENHANCED STORAGE STABILITY, AND ANHYDROSUGAR ALCOHOL STORAGE METHOD

TECHNICAL FIELD

The present invention relates to an anhydrosugar alcohol composition with improved storage stability and a method for storing anhydrosugar alcohol, and more specifically, to an anhydrosugar alcohol composition comprising anhydrosugar alcohol and amine-based additive and thus having improved storage stability, and a method capable of providing anhydrosugar alcohol of good quality wherein the storage of anhydrosugar alcohol is conducted in the presence of amine-based additive, thereby the storage stability of the anhydrosugar alcohol is remarkably improved.

BACKGROUND ART

Hydrogenated sugar (also referred to as "sugar alcohol") means a compound obtained by adding hydrogen to the reductive end group in sugar, and generally has a chemical formula of $HOCH_2(CHOH)_nCH_2OH$ wherein n is an integer of 2 to 5. According to the number of carbon atoms, hydrogenated sugar is classified into tetritol, pentitol, hexitol and heptitol (4, 5, 6 and 7 carbon atoms, respectively). Among them, hexitol having 6 carbon atoms includes sorbitol, mannitol, iditol, galactitol, etc. and in particular, sorbitol and mannitol are very useful materials.

Anhydrosugar alcohol has a diol form with two hydroxyl groups in the molecule, and can be produced by using hexitol derived from starch (for example, Korean Patent No. 10-1079518 and Korean Laid-open Patent Publication No. 10-2012-0066904). Because anhydrosugar alcohol is an environmentally friendly material derived from recyclable natural resources, it has received much interest for a long time and researches on its production continue to proceed. Among such anhydrosugar alcohols, isosorbide produced from sorbitol has the widest industrial applicability at present.

Anhydrosugar alcohol can be used in various fields including treatment of heart and blood vessel diseases, patch adhesive, medicaments such as mouthwash, etc., solvents for compositions in the cosmetics industry, emulsifiers in the food industry, etc. In addition, it can increase the glass transition temperature of polymer materials like polyester, PET, polycarbonate, polyurethane, epoxy resin, etc., and improve the strength of such materials. Furthermore, because anhydrosugar alcohol is an environmentally friendly material derived from natural resources, it is very useful in the plastics industry such as bioplastics and the like. It is also known that anhydrosugar alcohol can be used as an adhesive, environmentally friendly plasticizer, biodegradable polymer, and environmentally friendly solvent for water-soluble lacquer. As such, anhydrosugar alcohol is receiving much interest because of its wide applicability, and the level of practical industrial application thereof is increasing.

Anhydrosugar alcohol after purification and concentration has problems of the lowering of pH and the lowering of UV transmittance, particularly in summer with high temperature.

Korean Patent No. 10-0939431 introduces a technique of adding a reducing agent such as $NaBH_4$ or an antioxidant such as butylated hydroxy toluene (BHT, 2,6-di-t-butyl-4-methylphenol) to distilled anhydrosugar alcohol, in order to improve stability of the anhydrosugar alcohol. However, the storage stability of anhydrosugar alcohol is not improved sufficiently by this method, and thus it is difficult to prevent the lowering of pH and UV transmittance of anhydrosugar alcohol according to long term storage. In addition, additive such as morpholine is not preferable since it smells bad and thus exerts bad influence on workability and product quality.

CONTENTS OF THE INVENTION

Problems to be Solved

The purpose of the present invention is to provide an anhydrosugar alcohol composition with improved storage stability, showing no lowering of pH and UV transmittance even in long term storage at high temperature, and a method for storing anhydrosugar alcohol which can provide anhydrosugar alcohol of such a good quality.

Technical Means

In one aspect, the present invention provides an anhydrosugar alcohol composition, comprising anhydrosugar alcohol; and amine compound as additive for stabilization.

In another aspect, the present invention provides a method for storing anhydrosugar alcohol, wherein the anhydrosugar alcohol is mixed with amine compound as additive for stabilization and the storage thereof is conducted.

In still another aspect, the present invention provides anhydrosugar alcohol stored according to the above method, showing a transmittance of 90% or higher to ultraviolet (UV) light with 275 nm wavelength when diluted as an aqueous solution of 20% by weight concentration.

Effect of the Invention

According to the present invention, anhydrosugar alcohol showing no lowering of pH and UV transmittance even in long term storage at high temperature, for example, which shows a high UV transmittance of 90% or higher (with regard to 275 nm wavelength) and a stable pH of 6 to 8 when diluted as an aqueous solution of 20% by weight concentration, can be obtained easily.

CONCRETE MODE FOR CARRYING OUT THE INVENTION

The present invention is explained in more detail below.

In the present invention, 'hydrogenated sugar' is generally also referred to as 'sugar alcohol' and it means a compound obtained by adding hydrogen to the reductive end group in sugar. Hydrogenated sugar is classified according to the number of carbon atoms into tetritol, pentitol, hexitol and heptitol (4, 5, 6 and 7 carbon atoms, respectively). Among them, hexitol having 6 carbon atoms includes sorbitol, mannitol, iditol, galactitol, etc. and in particular, sorbitol and mannitol are very useful materials.

In the present invention, 'anhydrosugar alcohol' means any material that is obtained by removing one or more water molecules from the original structure of the hydrogenated sugar in any manner in one or more steps.

In the present invention, hexitol is preferably used as the hydrogenated sugar, and more preferably, hydrogenated sugar selected from sorbitol, mannitol, iditol or mixtures thereof is used, and even more preferably, sorbitol, which can be prepared easily through hydrogenation reaction of glucose derived from starch, is used.

In the present invention, the anhydrosugar alcohol is preferably dianhydrohexitol which is the dehydrated product of hexitol, and more preferably, the anhydrosugar alcohol is selected from isosorbide (1,4-3,6-dianhydrosorbitol), isomannide (1,4-3,6-dianhydromannitol), isoidide (1,4-3,6-dianhydroiditol) or mixtures thereof. Among them, isosorbide is particularly useful for industrial application.

The amine compound used as additive for stabilization in the present invention may be preferably a cyclic amine compound, and more concretely, it may be selected from monocyclic amine compound, bicyclic amine compound, fused polycyclic amine compound or combinations thereof.

According to a preferable embodiment of the present invention, the cyclic amine compound may comprise nitrogen atom only as heteroatom in its ring.

In an embodiment, the monocyclic amine compound may be, for example, a substituted or unsubstituted monocyclic amine compound having 3 to 10 of total ring atoms containing one or more (e.g., 1 to 3) nitrogen atoms. More concretely, the monocyclic amine compound may be selected from substituted or unsubstituted aziridine, azetidine, pyrrolidine, pyrazolidine, piperidine, piperazine, azepane, homopiperazine, azocane or combinations thereof.

In an embodiment, the bicyclic amine compound may have, for example, a structure wherein two (2) substituted or unsubstituted monocycles, each of which has 3 to 10 of total ring atoms containing one or more (e.g., 1 to 3) nitrogen atoms, are connected, where the two monocycles may be connected by direct bond or divalent linking group (e.g., alkylene group, and more concretely, $C_1$-$C_{10}$ alkylene group). More concretely, each of the two monocycles contained in the bicyclic amine compound may be independently selected from substituted or unsubstituted azetidine, pyrrolidine, piperidine, piperazine, azepane or homopiperazine.

In an embodiment, the fused polycyclic amine compound may be, for example, a substituted or unsubstituted fused polyheterocyclic amine compound having 8 to 15 of total ring atoms containing one or more (e.g., 1 to 3) nitrogen atoms, and more concretely, it may be selected from substituted or unsubstituted 1,4-diazabicyclo[2.2.2]octane, 1,8-diazabicycloundec-7-ene (DBU), 1,5-diazabicyclo[4.3.0]non-5-ene (DBN), 1,4-diazabicyclo[4.3.0]nonane, 2,8-diazabicyclo[4.3.0]nonane, 9-methyl-3,9-diazabicyclo[3.3.2]decane, quinuclidine or combinations thereof.

The cyclic amine compound may have, for example, one or more (e.g., 1 to 4) substituents selected from linear or branched alkyl (e.g., linear or branched $C_1$-$C_{10}$alkyl), cycloalkyl (e.g., $C_3$-$C_{10}$cycloalkyl), aminoalkyl (e.g., amino$C_1$-$C_{10}$alkyl), mono- or di-alkylaminoalkyl (e.g., mono- or di-$C_1$-$C_{10}$alkylamino$C_1$-$C_{10}$alkyl), carboxamide or amino.

In an embodiment, the amine compound may have a pKa of 8 to 15.

The amount of the amine compound as additive for stabilization in the anhydrosugar alcohol composition of the present invention, based on the weight of the anhydrosugar alcohol, may be 1 ppm or more, 2 ppm or more, 5 ppm or more, 8 ppm or more, or 10 ppm or more, and may be 300 ppm or less, 200 ppm or less, 100 ppm or less, 80 ppm or less, or 50 ppm or less, but it is not limited thereto.

In an embodiment, after long term storage at high temperature (for example, 10 days at 60° C.), the anhydrosugar alcohol composition of the present invention may show a transmittance of 90% or higher to ultraviolet (UV) light with 275 nm wavelength when diluted as an aqueous solution of 20% by weight concentration.

In addition, the final purity of the anhydrosugar alcohol composition of the present invention may be 99.5% by weight or more (e.g., 99.5% by weight to 99.7% by weight, or 99.5% by weight to 99.9% by weight) in case of solid phase, and may be 80% by weight or more (e.g., 80% by weight to 99% by weight, 80% by weight to 99.7% by weight, or 80% by weight to 99.9% by weight) in case of liquid phase.

In addition, after long term storage at high temperature (for example, 10 days at 60° C.), the anhydrosugar alcohol composition of the present invention may show a stable pH of 6 to 8 (e.g., measured at room temperature (25±3° C.)) when diluted as an aqueous solution of 20% by weight concentration.

In addition, the anhydrosugar alcohol composition of the present invention may be in liquid or solid form, and more concretely, in aqueous solution from (for example, aqueous solution with anhydrosugar alcohol concentration of 60% by weight or higher), pellet form, chip form or flake form, but it is not limited thereto.

The method for storing anhydrosugar alcohol of the present invention is characterized in conducting the storage of anhydrosugar alcohol mixed with the amine compound explained above as additive for stabilization, for example, in the amount explained above.

There is no special limitation to the anhydrosugar alcohol stored by the method of the present invention. According to an embodiment, the anhydrosugar alcohol stored by the method of the present invention may be that prepared by dehydration reaction of hydrogenated sugar.

There is no special limitation to the method of dehydrating hydrogenated sugar, and any method conventionally known in this field of art can be used as it is or with proper modification.

In dehydrating hydrogenated sugar and converting it to anhydrosugar alcohol, an acid catalyst is preferably used.

According to an embodiment, as the acid catalyst, one or more selected from the group consisting of sulfuric acid, nitric acid, hydrochloric acid, phosphoric acid, p-toluenesulfonic acid, methanesulfonic acid, ethanesulfonic acid, benzenesulfonic acid, naphthalenesulfonic acid or aluminum sulfate can be used, and preferably, sulfuric acid and other acid (for example, p-toluenesulfonic acid, methanesulfonic acid, ethanesulfonic acid, benzenesulfonic acid, naphthalenesulfonic acid or aluminum sulfate) can be mixed and used. The use amount of acid catalyst is preferably 0.5 to 10 parts by weight, based on 100 parts by weight of hydrogenated sugar (for example, hexitol).

The dehydration reaction of hydrogenated sugar may be conducted in the presence of acid catalyst as explained above at a temperature condition of 105° C. to 190° C. under a pressure condition of 1 mmHg to 100 mmHg for 1 hour to 10 hours, but it is not limited thereto.

In case of using acid catalyst in the dehydration reaction of hydrogenated sugar, the reaction product liquid is preferably neutralized with known alkali such as sodium hydroxide. The pH of the neutralized reaction product liquid is preferably 6 to 8. In addition, the product liquid of the dehydration reaction of hydrogenated sugar may be pretreated under heating/reduced pressure before feeding it into the subsequent treatment step (for example, distilling step) in order to remove moisture and a low-boiling-point substance(s) remaining in the dehydration reaction product liquid.

Preferably, the anhydrosugar alcohol stored by the method of the present invention is that obtained by distilling the dehydration reaction product liquid resulting from the dehydration reaction of hydrogenated sugar as explained above, purifying the distillation product, and then concentrating the purified product.

In an embodiment, the distillation may be conducted at a temperature condition of preferably from 100° C. to 250° C., more preferably from 100° C. to 200° C., and still more preferably from 110° C. to 170° C., and under a pressure condition of preferably 10 mmHg or less (e.g., 0.0001 to 10 mmHg, more concretely 0.0001 to 8 mmHg), more preferably 5 mmHg or less (e.g., 0.001 to 5 mmHg), and still more preferably 1 mmHg or less (e.g., 0.01 to 1 mmHg, more concretely 0.01 to 0.8 mmHg). If necessary, the distillation may be conducted through two or more steps. There is no special limitation to the method and device for the distillation, and any method and device conventionally known in this field of art may be utilized as it is or with proper modification. For example, a general condenser-type evaporator or column distillator may be used, or a thin-film evaporator may be utilized for the distillation.

In an embodiment, the purification may be conducted by one or more processes selected from crystallization, decolorization, cation exchange resin treatment or anion exchange resin treatment. In a purification process of a preferable embodiment, crystallization of the distillation product, decolorization of the crystallization product, and cation exchange resin treatment followed by anion exchange resin treatment of the decolorization product can be conducted subsequently.

There is no special limitation to the method and device for the crystallization, and any crystallization method and device conventionally known in this field of art may be utilized as it is or with proper modification. For example, concretely, it is possible to use a method of dissolving anhydrosugar alcohol in a solvent such as water, ethyl acetate, acetone, toluene, benzene, xylene, alcohol, etc. at an elevated temperature if necessary, and then lowering the temperature of the solution to precipitate the anhydrosugar alcohol crystals, or a method of melt crystallization using no solvent may be used.

The decolorization can be conducted by contacting an aqueous solution, where the crystallite of anhydrosugar alcohol is dissolved in water (for example, distilled water), with active carbon. As the active carbon, one or more selected from active carbon groups obtained by activating a plant source such as wooden material, palm, etc. or a mineral source such as brown coal, bituminous coal, soft coal, anthracite coal, etc. may be used. The average particle size of the active carbon is preferably from 0.25 to 1.0 mm, and more preferably from 0.25 mm to 0.70 mm. There is no special limitation in the manner of contacting the aqueous solution of anhydrosugar alcohol with active carbon. For example, the contact may be conducted in a manner of passing the aqueous solution of anhydrosugar alcohol through a column packed with the active carbon, or it may alternatively be conducted in a manner of incorporating the aqueous solution of anhydrosugar alcohol and the active carbon into a reactor and mixing them with agitation for a given time.

The cation exchange resin treatment may be accomplished by contacting the decolorization product liquid with cation exchange resin, and this may be conducted in a manner of passing the decolorization product liquid through a column packed with cation exchange resin. As the cation exchange resin, all of strong cation exchange resin (e.g., TRILITE-SCR-B) and weak cation exchange resin (e.g., DIAION WK11) may be used, and strong cation exchange resin is preferably used. As the strong cation exchange resin, one or more selected from H-form strong cation exchange resin (e.g., TRILITE-SCR-BH) or Na-form strong cation exchange resin (e.g., TRILITE-SCR-B) may be used preferably.

The anion exchange resin treatment may be conducted in a manner of passing the cation exchange resin treatment product liquid through a column packed with anion exchange resin. As the anion exchange resin, all of strong anion exchange resin (e.g., TRILITE AMP24) and weak anion exchange resin (e.g., DIAION WA10) may be used, and strong anion exchange resin is preferably used. As the strong anion exchange resin, Cl-form strong anion exchange resin (e.g., TRILITE AMP24) may be used preferably.

In an embodiment, the concentration may be conducted at a temperature of 90° C. to 110° C. under a pressure condition of 10 mmHg to 100 mmHg for 30 minutes or longer (e.g., 30 minutes to 4 hours), but it is not limited thereto. The concentration may be conducted in a conventional concentration device (for example, rotary evaporator, forced circulation evaporator, thin film evaporator).

In an embodiment, after long term storage at high temperature (for example, 10 days at 60° C.), the anhydrosugar alcohol stored according to the present invention may show a transmittance of 90% or higher to ultraviolet (UV) light with 275 nm wavelength when diluted as an aqueous solution of 20% by weight concentration.

In addition, after long term storage at high temperature (for example, 10 days at 60° C.), the anhydrosugar alcohol stored according to the present invention may show a stable pH of 6 to 8 (e.g., measured at room temperature (25±3° C.)) when diluted as an aqueous solution of 20% by weight concentration.

In addition, the anhydrosugar alcohol stored according to the present invention may be in liquid or solid form, and more concretely, in aqueous solution from (for example, aqueous solution with anhydrosugar alcohol concentration of 60% by weight or higher), pellet form, chip form or flake form, but it is not limited thereto.

The present invention is explained in more detail through the following Examples and Comparative Examples. However, the Examples are intended to facilitate understanding of the present invention only, and the scope of the present invention is not limited thereby.

EXAMPLES AND COMPARATIVE EXAMPLES

Preparation Example 1,200 g of sorbitol powder (D-sorbitol, Samyang Genex Inc.) was fed into a four-neck glass reactor equipped with an agitator and melted by heating to 110° C. 12 g of concentrated sulfuric acid (Duksan Chemical, 95%) and 7.2 g of methanesulfonic acid (Sigma, 70%) were added thereto, and the reaction mixture was heated to 135° C. In maintaining this temperature, dehydration reaction was conducted for 4 hours under a vacuum condition of 40 torr to convert the starting material, sorbitol, to the anhydrosugar alcohol, isosorbide. After the dehydration reaction, the reaction mixture was cooled to 110° C., and 31.2 g of 50% sodium hydroxide solution (Samjeon Pure Chemical) was added thereto for neutralization.

The neutralized anhydrosugar alcohol was distilled by using a thin-film evaporator at 180° C. under vacuum of 5 mmHg or less. The purity of the obtained anhydrosugar alcohol distillate was 97.5%.

The obtained distillate was placed in a jacketed reaction bath and 300 g of acetone (Samjeon Pure Chemical) was added thereto, and the crystallization was carried out in cooling the mixture to 0° C. After the crystallization was finished and then dehydration was conducted, the anhydrosugar alcohol crystals were separated from the mother liquid and recovered.

The obtained crystals were dissolved by adding distilled water thereto, and a solution with solid content of 37% was prepared. The prepared solution was decolorized by passing it through a column packed with fine granular active carbon having average particle size of 0.25 mm at the rate of 1.0 BV/h (bed volume/hour), and the decolorized anhydrosugar alcohol was then passed through a column packed with H-form strong cation exchange resin (TRILITE-SCR-BH, Samyang Corporation) at the rate of 1.5 BV/h, and the resulting liquid was then passed through a column packed with Cl-form strong anion exchange resin (TRILITE AMP24, Samyang Corporation) at the rate of 1.5 BV/h, to obtain the finally purified anhydrosugar alcohol.

1,000 g of aqueous solution of 40% by weight of the purified anhydrosugar alcohol was fed into a 2 L rotary evaporator and concentrated. The concentration was conducted with adjusting the temperature to 100° C. and the vacuum degree to 20 mmHg for 2 hours.

Example 1

A reactor with heatable jacket was maintained to 80° C., and thereto 1,000 g of the concentrated anhydrosugar alcohol (water content: 0.3% by weight) obtained in the above Preparation Example was fed and melted with agitation. The pH of the aqueous solution of 20% by weight of the melted anhydrosugar alcohol was 5.8. To this reactor, 10 mg of 2,2,6,6-tetramethylpiperidine (TMP) (10 ppm based on the weight of anhydrosugar alcohol) was added and agitated for 5 minutes, and the resulting product was cooled to obtain anhydrosugar alcohol in solid phase. The aqueous solution of 20% by weight of the obtained solid anhydrosugar alcohol showed pH of 6.3 measured at room temperature (25±3° C.) and UV transmittance of 95% measured by using 5 cm quartz cell at 275 nm.

The solid anhydrosugar alcohol obtained above was divided and put into 20 mL glass vials, and then stored in a dryer at 60° C. for 10 days in air-contacting condition, and thereafter the changes in pH and UV transmittance were measured. The anhydrosugar alcohol (aqueous solution of 20% by weight) after the storage at 60° C. for 10 days showed pH of 6.2 measured at room temperature and UV transmittance of 91% measured by using 5 cm quartz cell at 275 nm, which means that the storage stability was very good.

Example 2

Excepting that 20 mg of 1,5-diazabicyclo[4.3.0]non-5-ene (DBN) (20 ppm based on the weight of anhydrosugar alcohol) was used as an amine-based additive instead of TMP, the same process as Example 1 was carried out to obtain anhydrosugar alcohol in solid phase. The aqueous solution of 20% by weight of the obtained solid anhydrosugar alcohol showed pH of 8.1 measured at room temperature and UV transmittance of 93% measured by using 5 cm quartz cell at 275 nm.

The solid anhydrosugar alcohol obtained above was stored at 60° C. for 10 days in the same manner as Example 1, and after the storage, the anhydrosugar alcohol (aqueous solution of 20% by weight) showed pH of 7.8 measured at room temperature and UV transmittance of 91% measured by using 5 cm quartz cell at 275 nm, which means that the storage stability was very good.

Example 3

Excepting that 40 mg of 1,8-diazabicycloundec-7-ene (DBU) (40 ppm based on the weight of anhydrosugar alcohol) was used as an amine-based additive instead of TMP, the same process as Example 1 was carried out to obtain anhydrosugar alcohol in solid phase. The aqueous solution of 20% by weight of the obtained solid anhydrosugar alcohol showed pH of 7.9 measured at room temperature and UV transmittance of 94% measured by using 5 cm quartz cell at 275 nm.

The solid anhydrosugar alcohol obtained above was stored at 60° C. for 10 days in the same manner as Example 1, and after the storage, the anhydrosugar alcohol (aqueous solution of 20% by weight) showed pH of 7.3 measured at room temperature and UV transmittance of 90% measured by using 5 cm quartz cell at 275 nm, which means that the storage stability was very good.

Comparative Example 1

Excepting that 50 mg of ascorbic acid—an antioxidant—(50 ppm based on the weight of anhydrosugar alcohol) was used as an additive instead of TMP, the same process as Example 1 was carried out to obtain anhydrosugar alcohol in solid phase. The aqueous solution of 20% by weight of the obtained solid anhydrosugar alcohol showed pH of 4.5 measured at room temperature and UV transmittance of 93% measured by using 5 cm quartz cell at 275 nm.

The solid anhydrosugar alcohol obtained above was stored at 60° C. for 10 days in the same manner as Example 1, and after the storage, the anhydrosugar alcohol (aqueous solution of 20% by weight) showed pH of 3.0 measured at room temperature and UV transmittance of 51% measured by using 5 cm quartz cell at 275 nm, which means that there was no effect of improving the storage stability.

Comparative Example 2

Excepting that 20 mg of 1-methylimidazole (pKa: 6.95)—an antioxidant—(20 ppm based on the weight of anhydrosugar alcohol) was used as an additive instead of TMP, the same process as Example 1 was carried out to obtain anhydrosugar alcohol in solid phase. The aqueous solution of 20% by weight of the obtained solid anhydrosugar alcohol showed pH of 7.3 measured at room temperature and UV transmittance of 94% measured by using 5 cm quartz cell at 275 nm.

The solid anhydrosugar alcohol obtained above was stored at 60° C. for 10 days in the same manner as Example 1, and after the storage, the anhydrosugar alcohol (aqueous solution of 20% by weight) showed pH of 3.0 measured at room temperature and UV transmittance of 35% measured by using 5 cm quartz cell at 275 nm, which means that there was no effect of improving the storage stability.

Comparative Example 3

Excepting that TMP was not used, the same process as Example 1 was carried out to obtain anhydrosugar alcohol in solid phase. The aqueous solution of 20% by weight of the obtained solid anhydrosugar alcohol showed pH of 5.5 measured at room temperature and UV transmittance of 95% measured by using 5 cm quartz cell at 275 nm.

The solid anhydrosugar alcohol obtained above was stored at 60° C. for 10 days in the same manner as Example 1, and after the storage, the anhydrosugar alcohol (aqueous solution of 20% by weight) showed pH of 3.2 measured at room temperature and UV transmittance of 40% measured by using 5 cm quartz cell at 275 nm, which means that there was no effect of improving the storage stability.

The invention claimed is:

1. A composition comprising
   a concentrated anhydrosugar alcohol; and
   an amine compound as an additive for stabilization;
   wherein the concentrated anhydrosugar alcohol is dianhydrohexitol in solid form,
   wherein the amine compound is selected from the group consisting of piperidine, 1,8-diazabicycloundec-7-ene, 1,5-diazabicyclo[4.3.0]non-5-ene and combinations thereof, each of which is unsubstituted or substituted with one or more substituents selected from the group consisting of linear or branched $C_1$-$C_{10}$alkyl, $C_3$-$C_{10}$cycloalkyl, amino$C_1$-$C_{10}$alkyl, mono- or di-$C_1$-$C_{10}$alkylamino$C_1$-$C_{10}$alkyl, carboxamide and amino, and
   wherein an amount of the amine compound is 1 ppm or more and 300 ppm or less, based on a weight of the concentrated anhydrosugar alcohol.

2. The composition of claim 1, wherein the amine compound has a pKa of 8 to 15.

3. The composition of claim 1, which shows a transmittance of 90% or higher to ultraviolet (UV) light with 275 nm wavelength when diluted as an aqueous solution of 20% by weight concentration.

4. The composition of claim 1, which shows a pH of 6 to 8 when diluted as an aqueous solution of 20% by weight concentration.

5. A method for storing concentrated anhydrosugar alcohol, wherein the concentrated anhydrosugar alcohol is mixed with an amine compound as an additive for stabilization and the storage thereof is conducted,
   wherein the concentrated anhydrosugar alcohol is dianhydrohexitol in solid form,
   wherein the amine compound is selected from the group consisting of piperidine, 1,8-diazabicycloundec-7-ene, 1,5-diazabicyclo[4.3.0]non-5-ene and combinations thereof, each of which is unsubstituted or substituted with one or more substituents selected from the group consisting of linear or branched $C_1$-$C_{10}$alkyl, $C_3$-$C_{10}$cycloalkyl, amino$C_1$-$C_{10}$alkyl, mono- or di-$C_1$-$C_{10}$alkylamino$C_1$-$C_{10}$alkyl, carboxamide and amino, and
   wherein an amount of the amine compound mixed with the concentrated anhydrosugar alcohol is 1 ppm or more and 300 ppm or less, based on a weight of the concentrated anhydrosugar alcohol.

6. The method for storing concentrated anhydrosugar alcohol of claim 5, wherein the concentrated anhydrosugar alcohol stored is that obtained by distilling a dehydration reaction product liquid resulting from dehydration reaction of hexitol, purifying the distillation product, and then concentrating the purified product.

7. The method for storing concentrated anhydrosugar alcohol of claim 6, wherein an acid catalyst is used in the dehydration reaction of hexitol.

8. The method for storing concentrated anhydrosugar alcohol of claim 6, wherein the distillation is conducted by using a thin-film evaporator.

9. The method for storing concentrated anhydrosugar alcohol of claim 6, wherein the purification is conducted by one or more processes selected from crystallization, decolorization, cation exchange resin treatment or anion exchange resin treatment.

10. The method for storing concentrated anhydrosugar alcohol of claim 6, wherein in the purification, crystallization of the distillation product, decolorization of the crystallization product, and cation exchange resin treatment followed by anion exchange resin treatment of the decolorization product are conducted subsequently.

11. The method for storing concentrated anhydrosugar alcohol of claim 6, wherein the concentration is conducted at a temperature of 90° C. to 110° C. under a pressure condition of 10 mmHg to 100 mmHg for 30 minutes or longer.

* * * * *